US008880188B2

(12) United States Patent
Wahlstrand et al.

(10) Patent No.: US 8,880,188 B2
(45) Date of Patent: Nov. 4, 2014

(54) IMPLANTABLE MEDICAL LEADS AND SYSTEMS THAT UTILIZE REFLECTION POINTS TO CONTROL INDUCED RADIO FREQUENCY ENERGY

(75) Inventors: Carl D. Wahlstrand, North Oaks, MN (US); Thomas B. Hoegh, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/981,577

(22) PCT Filed: Jan. 27, 2012

(86) PCT No.: PCT/US2012/022868
§ 371 (c)(1),
(2), (4) Date: Oct. 24, 2013

(87) PCT Pub. No.: WO2012/103419
PCT Pub. Date: Aug. 2, 2012

(65) Prior Publication Data
US 2014/0052227 A1  Feb. 20, 2014

Related U.S. Application Data

(60) Provisional application No. 61/437,345, filed on Jan. 28, 2011.

(51) Int. Cl.
*A61N 1/00* (2006.01)
*A61N 1/05* (2006.01)
*A61N 1/08* (2006.01)

(52) U.S. Cl.
CPC .. *A61N 1/08* (2013.01); *A61N 1/05* (2013.01); *A61N 2001/086* (2013.01)
USPC .............................. 607/116; 607/36; 607/37

(58) Field of Classification Search
USPC .............................................. 607/36–37, 116
See application file for complete search history.

(56) References Cited

U.S. PATENT DOCUMENTS 6,971,391 B1   12/2005   Wang et al.
7,127,294 B1   10/2006   Wang et al.
(Continued)

FOREIGN PATENT DOCUMENTS

WO    2009134901 A1    11/2009
WO    WO2009134901   *  11/2009   ............... A61N 1/16

OTHER PUBLICATIONS

PCT/US2012/022868—International Search Report and Written Opinion, Aug. 16, 2012.

*Primary Examiner* — Nicole F Lavert (57) ABSTRACT

Implantable medical leads and systems that include lead utilize reflection points within the lead to control radio frequency current that has been induced onto one or more filars within the lead. The radio frequency current may be controlled by the reflection points to block at least some of the radio frequency current from reaching an electrode of the lead and to dissipate at least some of the radio frequency current as heat on the filar. Controlling the radio frequency current thereby reduces the amount that is dissipated into bodily tissue through one or more electrodes of the lead and reduces the likelihood of tissue damage. The reflection points may be created by physical changes such as to material or size in the filar and/or in insulation layers that may be present such as an inner jacket about the filar and an outer jacket formed by the body of the lead.

28 Claims, 5 Drawing Sheets

(56) References Cited

U.S. PATENT DOCUMENTS

| | | |
|---|---|---|
| 2005/0222657 A1 | 10/2005 | Wahlstrand et al. |
| 2006/0009819 A1 | 1/2006 | Pryzbyszewski |
| 2010/0100164 A1 | 4/2010 | Johnson et al. |
| 2010/0312294 A1* | 12/2010 | Martinez et al. ............. 607/2 |
| 2011/0015713 A1 | 1/2011 | Min |

* cited by examiner

IMPLANTABLE MEDICAL LEADS AND SYSTEMS THAT UTILIZE REFLECTION POINTS TO CONTROL INDUCED RADIO FREQUENCY ENERGY

TECHNICAL FIELD

Embodiments are related to implantable medical leads and systems including implantable medical leads that may carry induced radio frequency energy. More particularly, embodiments are related to implantable medical leads and related systems that include reflection points to control the induced radio frequency energy.

BACKGROUND

Implantable medical systems include an implantable medical device connected to an implantable medical lead. The implantable medical device is used to produce stimulation signals for delivery to tissue of a patient and/or to sense physiological signals from the tissue of the patient. The implantable medical lead includes electrical contacts on a proximal end that are connected to electrical connectors within the medical device. Electrodes are present on a distal end of the implantable medical lead to contact the tissue at the stimulation site. Filars are present within the lead to carry electrical signals between the contacts at the proximal end and the electrodes at the distal end.

The implantable medical leads can present an issue for a patient who may need to undergo a magnetic resonance imaging (MRI) scan. An MRI scan exposes the patient to radio frequency (RE) electromagnetic energy. This RF energy may be collected by the filars in the form of induced RF electrical current during the MRI scan. This RE electrical current may be delivered to the tissue of the patient via the electrodes at the distal end.

The RF electrical current induced onto the filars presents a serious condition. The electrode is a relatively small amount of surface area such that the RF electrical current from a given electrode is dissipated into a relatively small amount of tissue which may heat the tissue by an excessive amount that causes tissue damage. Furthermore, the electrode may be located adjacent to sensitive tissue such as within the brain or spine where tissue damage from the excessive heating by the induced RF current may have severe consequences.

SUMMARY

Embodiments address issues such as these and others by providing implantable medical leads and implantable medical systems where the implantable medical leads include reflection points that control the radio frequency energy induced onto the filars. The reflection points may be present on the filar(s) or on the insulation layer(s) such as on an inner jacket formed about individual filars or on an outer jacket of the lead. The reflection points may be created in various ways such as changing physical dimensions like the diameter at a given point or by changing the materials that are present at a given point.

Embodiments provide implantable medical systems and leads. The implantable medical lead includes an outer jacket and a filar located within the outer jacket. The filar includes physical changes that establish multiple radio frequency reflection points located along the length of the filar. The implantable medical lead further includes a proximal contact and a distal electrode, with the filar interconnecting the proximal contact to the distal electrode.

Embodiments provide other implantable medical systems and leads. The implantable medical lead includes an outer jacket and a filar surrounded by an inner jacket. The filar and inner jacket are located within the outer jacket, and the inner jacket includes physical changes that establish multiple radio frequency reflection points located along the length of the filar. The implantable medical lead further includes a proximal contact and a distal electrode, with the filar interconnecting the proximal contact to the distal electrode.

Embodiments provide additional implantable medical systems and leads. The implantable medical lead includes an outer jacket and a filar being located within the outer jacket such that the outer jacket includes physical changes that establish multiple radio frequency reflection points located along the length of the filar at non-standard intervals of repetition. The implantable medical lead further includes a proximal contact and a distal electrode, with the filar interconnecting the proximal contact to the distal electrode.

Embodiments provide other implantable medical systems and leads. The implantable medical lead includes an outer jacket and a filar being located within the outer jacket. Discrete circuit elements are electrically coupled to the filar and establish multiple radio frequency reflection points located along the length of the filar at nonstandard intervals of repetition. The implantable medical lead includes a proximal contact and a distal electrode, with the filar interconnecting the proximal contact to the distal electrode.

DETAILED DESCRIPTION

Embodiments provide implantable medical leads and systems that include reflection points along the leads to control RF energy that is induced as RE current onto mars of the leads. The reflection points may be present on the filar or on other elements of the lead such as an inner jacket around the individual filar or an outer jacket that may form the outer body of the lead. The reflection points may be created by physical changes such as a change in diameter of the filar or insulator or a change in the materials that are used for the filar or insulator that produce a change in a characteristic impedance of the lead.

Figure 1:
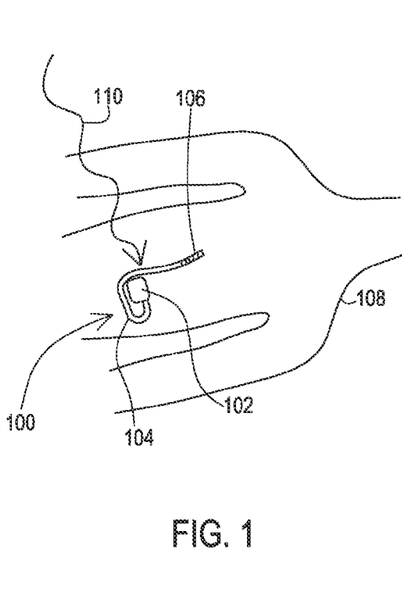
FIG. 1 shows a patient with an implantable medical system in the presence of RE electromagnetic energy.

FIG. 1 shows an environment where an implantable medical system 100 has been implanted within a patient 108. The implantable medical system 100 includes an implantable medical device (IMD) 102 and an implantable medical lead 104. The implantable medical lead 104 is connected to the IMD 102 at a proximal end, and the lead 104 extends to a stimulation site where electrodes 106 on the distal end are present to electrically interface with the tissue of the patient 108.

The patient 108 is being exposed to RF electromagnetic energy 110. This RE energy 110 encounters the implantable medical system 100 and may induce RF current onto the lead 106. However, the lead 106 may include reflection points positioned at various locations to reflect the RF current away from the electrodes and to cause at least some of the RF current to dissipate as heat over the filar(s) present within the lead 104 rather than exiting through the electrodes 106.

Figure 2:
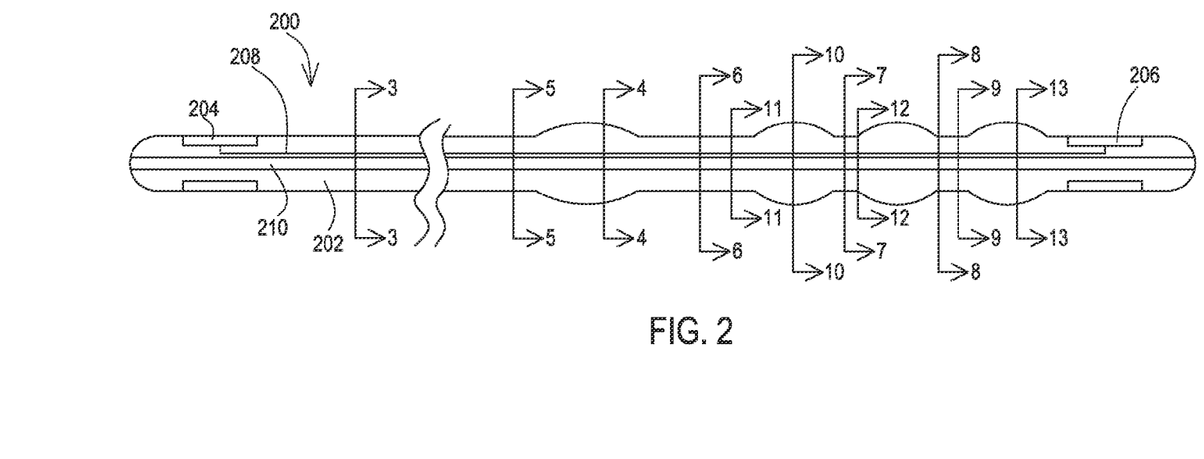
FIG. 2 shows an example of a longitudinal cross-section of an implantable medical lead having reflection points provided by changes in filar diameter, filar material, inner jacket diameter, inner jacket material, outer jacket diameter, and outer jacket material.

FIG. 2 shows a longitudinal cross-section of an example of a lead 200 with reflection points. This lead 200 is shown with a single contact 204, single filar 208, and single electrode 206. It will be appreciated that any number of contacts, filars, and electrodes may be present and may benefit from the reflection points. In this particular example, the lead 200 includes a body 202 which may be established by the outer jacket, or the outer jacket may be an outer layer adhered to the body 202. The body 202 defines a lumen 210 that may be present to receive a stylet that guides the lead 200 during implantation and is removed thereafter.

The body 202 forming the outer jacket may be made of various materials. Examples include elasthane, silicone, other polymers and the like. Likewise, the filar 208 may be made of various materials such as MP35N®, alloy, platinum, silver cored MP35N® alloy, and the like.

Additionally, the lead 200 may include an inner jacket that is not shown in FIG. 2 but adheres to the outer surface of the filar 204 and isolates the filar 204 from the body 202. The inner jacket may also be made of various materials. Examples include ethylene tetrafluoroethylene (ETFE), other polymers, and the like.

Figure 3:
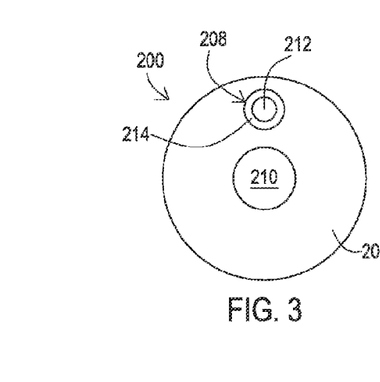
FIG. 3 shows a first lateral cross-section of the implantable medical lead of FIG. 2 at a reference point.

The physical parameters including the dimensions and the types of material used for each of the components within the lead 200 such as the outer jacket of the body 202, the inner jacket, and the filar 206 contribute to the characteristic impedance of the filar 202. To create a reflection point, the characteristic impedance is altered at a given location where the reflection point is desired. To alter the characteristic impedance and thereby create the reflection point, a physical change is present in either a dimension or a material for the particular component. Examples of such physical changes are present in this example of the lead 200, where cross-section 3-3 shown in FIG. 3 is a reference point showing the normal construction where a reflection point is not present. Cross-sections 4-4 through 13-13 show examples of some of the other reflection points that are present in this example of the lead 200.

FIG. 3 shows a lateral cross-section taken through 3-3 of FIG. 2. Here, the elements of the lead 200 including the body 202 forming the outer jacket, the filar 212, and the inner jacket 208 on the filar 212 are normal in that this represents the configuration of the areas of the lead where no reflection point is present. In the example of FIG. 2, this cross-section taken through 3-3 is in a normal portion near the proximal end of the lead 200. It will be appreciated that normal portions such as this that may extend for significant portions of the lead may appear at any point along the lead from proximal tip to distal tip.

Figure 4:
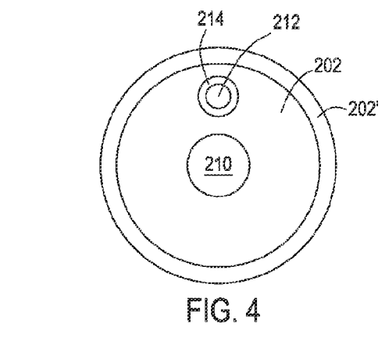
FIG. 4 shows a second lateral cross-section of the implantable medical lead of FIG. 2 at a first reflection point.

FIG. 4 shows a lateral cross-section taken through 4-4 of FIG. 2 where a reflection point is present. Here, the body 202 forming the outer jacket includes additional material 202' creating a larger diameter over a particular length of the lead 200. The additional material 202' may be the same or different material than the body 202. The other elements including the filar 212 and inner jacket 214 have not changed. The change in diameter results in a change to the characteristic impedance of the filar 202 thereby producing a reflection point. It will be appreciated that rather than increasing the diameter, the body 202' forming the outer jacket may have a reduced diameter to create a reflection point.

An alternative to the layer 202' being an additional jacket material, 202 may represent a floating electrode. In this case, the floating electrode may be attached to the body 202 in the same manner as the electrode 206 that is used for stimulation, but the floating electrode is not connected to a filar 212. The floating electrode presents a physical change to the outer jacket that creates a change in the characteristic impedance of the filar 212 such that the presence of the floating electrode creates a reflection point. In some examples, the floating electrode present at any given reflection point may be capacitively coupled to one or more of the filars within the lead 200.

Figure 5:
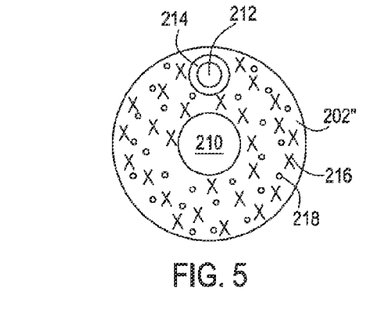
FIG. 5 shows a third lateral cross-section of the implantable medical lead of FIG. 2 at a second reflection point.

FIG. 5 shows a lateral cross-section taken through 5-5 of FIG. 2 where a reflection point is present. Here, the body 202 forming the outer jacket includes one or more types of dopant materials. In this particular example, two dopant materials 216 and 218 are present and create a change in the conductance of the outer jacket over a particular length of the lead 200. Examples of dopant materials include metals such as titanium, stainless steel, platinum, and the like. The other elements including the filar 212 and inner jacket 214 have not changed. The change in material results in a change to the characteristic impedance of the filar 202 thereby producing a reflection point.

Figure 6:
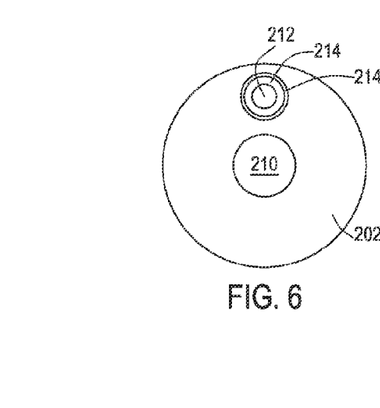
FIG. 6 shows a fourth lateral cross-section of the implantable medical lead of FIG. 2 at a third reflection point.

FIG. 6 shows a lateral cross-section taken through 6-6 of FIG. 2 where a reflection point is present. Here, the body 202 forming the outer jacket is normal in size and material. However, the inner jacket 214 includes additional material 214' creating a larger diameter over a particular length of the lead 200. The additional material 214' may be the same or different material than the material of the inner jacket 214. The other elements including the filar 212 and body 202 forming the outer jacket have not changed. The change in diameter results in a change to the characteristic impedance of the filar 202 thereby producing a reflection point. It will be appreciated that rather than increasing the diameter, the inner jacket 214' may have a reduced diameter to create a reflection point.

Figure 7:
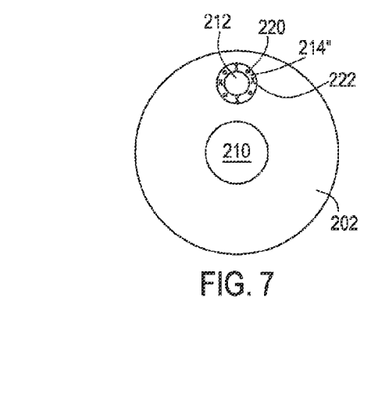
FIG. 7 shows a fifth lateral cross-section of the implantable medical lead of FIG. 2 at a fourth reflection point.

FIG. 7 shows a lateral cross-section taken through 7-7 of FIG. 2 where a reflection point is present. Here, the body 202 forming the outer jacket is normal in size and material. However, the inner jacket 214' includes at least one type of dopant material. In this particular example, two dopant materials 220 and 222 are present and create a change in the conductance of the outer jacket over a particular length of the lead 200. Examples of these dopant materials also include titanium, stainless steel, platinum, and the like. The other elements including the filar 212 and body 202 forming the outer jacket have not changed. The change in materials results in a change to the characteristic impedance of the filar 202 thereby producing a reflection point.

Figure 8:
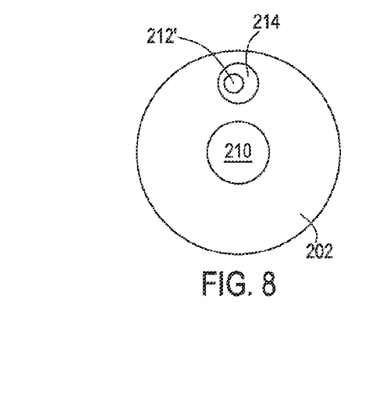
FIG. 8 shows a sixth lateral cross-section of the implantable medical lead of FIG. 2 at a fifth reflection point.

FIG. 8 shows a lateral cross-section taken through 8-8 of FIG. 2 where a reflection point is present. Here, both the body 202 forming the outer jacket and the inner jacket 214 are normal in diameter and material. However, the filar 212' has a reduced diameter, such as by creating a crimp and the inner jacket 214 may fill in the area of reduced diameter.

The change in diameter of the filar 212' at the area of this cross-section results in a change to the characteristic impedance of the filar 202 thereby producing a reflection point. It will be appreciated that rather than reducing the diameter, the filar 212' may have an increased diameter to create a reflection point such as by welding additional material onto the filar 212'.

Figure 9:
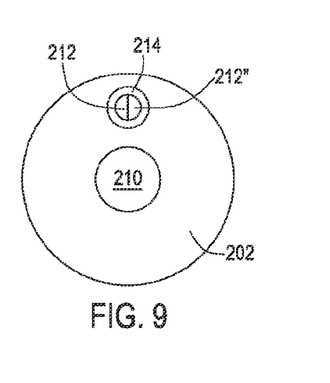
FIG. 9 shows a seventh lateral cross-section of the implantable medical lead of FIG. 2 at a sixth reflection point.

FIG. 9 shows a lateral cross-section taken through 9-9 of FIG. 2 where a reflection point is present. Here, both the body 202 forming the outer jacket and the inner jacket 214 are normal in diameter and material. However, the filar 212 has a change in material by the addition of a material 212" adjacent to the material 212, such as by welding a different material 212" onto the existing filar 212. It should be noted that both materials define the surface, which may provide a more effective reflection point than using an approach with a core considering that the RF induced current is primarily on the surface due to the skin effect. If the filar diameter is to be maintained as shown in FIG. 9, the existing filar material may have a reduced filar diameter while the new filar material increases the filar diameter back to the normal level. The change in material of the filar 212" at the area of this cross-section results in a change to the characteristic impedance of the filar 202 thereby producing a reflection point.

FIGS. 4-9 have shown examples where a single parameter such as size or material has changed to produce a reflection point. FIGS. 10-13 show examples where multiple parameters have changed to produce for each of the reflection points.

Figure 10:
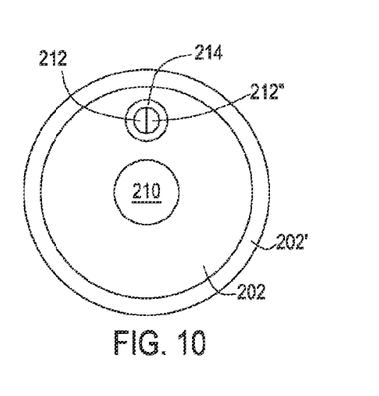
FIG. 10 shows an eighth lateral cross-section of the implantable medical lead of FIG. 2 at a seventh reflection point.

FIG. 10 shows a lateral cross-section taken through 10-10 of FIG. 2 where a reflection point is present. Here, the inner jacket 214 is normal in diameter and material. However, the filar 212" has a change in material while the diameter may be the same or different, such as by welding a different material onto the existing filar 212. Additionally, the body 202 forming the outer jacket has additional material 202' that increases the diameter of the body 202. The combination of the change in material of the filar 212" as well as the diameter of the outer jacket 202' at the area of this cross-section results in a change to the characteristic impedance of the filar 202 thereby producing a reflection point. It will be appreciated that the multiple parameters relating to the filar 212 and the body 202 forming the outer jacket may have additionally or alternatively included other changes such as a reduced diameter of the body 202' forming the outer jacket, a change to the diameter of the filar 212, and/or a change to the material of the body 202, 202' forming the outer jacket.

Figure 11:
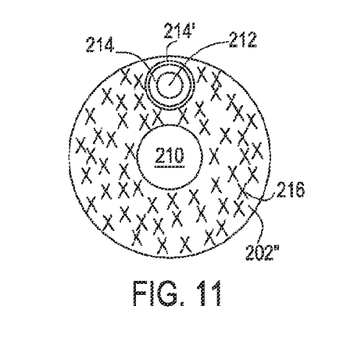
FIG. 11 shows a ninth lateral cross-section of the implantable medical lead of FIG. 2 at an eighth reflection point.

FIG. 11 shows a lateral cross-section taken through 11-11 of FIG. 2 where a reflection point is present. Here, the body 202 forming the outer jacket includes one or more types of dopant materials. In this particular example, one dopant material 216 is present. Additionally, the inner jacket 214 includes additional material 214' increasing the diameter of the inner jacket. The combination of the change in material of the body 202 forming the outer jacket and the change in diameter of the inner jacket 214 results in a change to the characteristic impedance of the filar 202 thereby producing a reflection point. It will be appreciated that the multiple parameters relating to the body 202 forming the outer jacket and the inner jacket may have additionally or alternatively included other changes such as a change in diameter of the body 202 forming the outer jacket, a reduced diameter of the inner jacket 214, and/or a change in the material of the inner jacket 214.

Figure 12:
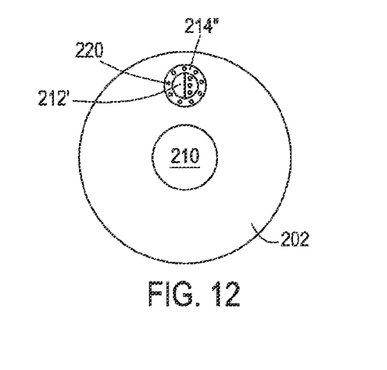
FIG. 12 shows a tenth lateral cross-section of the implantable medical lead of FIG. 2 at a ninth reflection point.

FIG. 12 shows a lateral cross-section taken through 12-12 of FIG. 2 where a reflection point is present. Here, the inner jacket 214" includes one or more dopant materials. In this particular example, one dopant material 220 is present. Additionally, the filar 212' has a reduced diameter. The combination of the change in material of the inner jacket 214" and the change in diameter of the filar 212' results in a change to the characteristic impedance of the filar 202 thereby producing a reflection point. It will be appreciated that the multiple parameters relating to the inner jacket and filar may have additionally or alternatively included other changes such as a change in diameter of the inner jacket 214", a change in diameter of the inner jacket 214", and/or a change in the material of the inner jacket 214.

Figure 13:
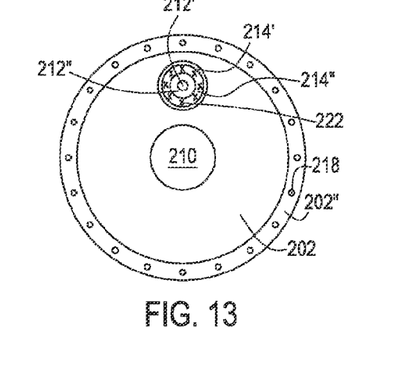
FIG. 13 shows an eleventh lateral cross-section of the implantable medical lead of FIG. 2 at a tenth reflection point.

FIG. 13 shows a lateral cross-section taken through 13-13 of FIG. 2 where a reflection point is present. Here, the inner jacket 214" includes one or more dopant materials. In this particular example, one dopant material 222 is present. The inner jacket 214" also includes additional material 214' increasing the diameter of the inner jacket. Additionally, the filar 212' has a reduced diameter while also including a different material 212" welded onto the existing reduced diameter portion 212'. The body 202 firming the outer jacket includes additional material 202" that increases the diameter of the body 202 forming the outer jacket. Furthermore, the additional material 202" is doped with one or more dopants, in this case a single dopant type 218. The combination of the change in materials and sizes of the inner jacket 214', 214", the filar 212', 212", and the body 202, 202" forming the outer jacket result in a change to the characteristic impedance of the filar 202 thereby producing a reflection point. It will be appreciated that the multiple parameters relating to the body forming the outer jacket, the inner jacket and the filar may have additionally or alternatively included other changes as well.

Figure 14:
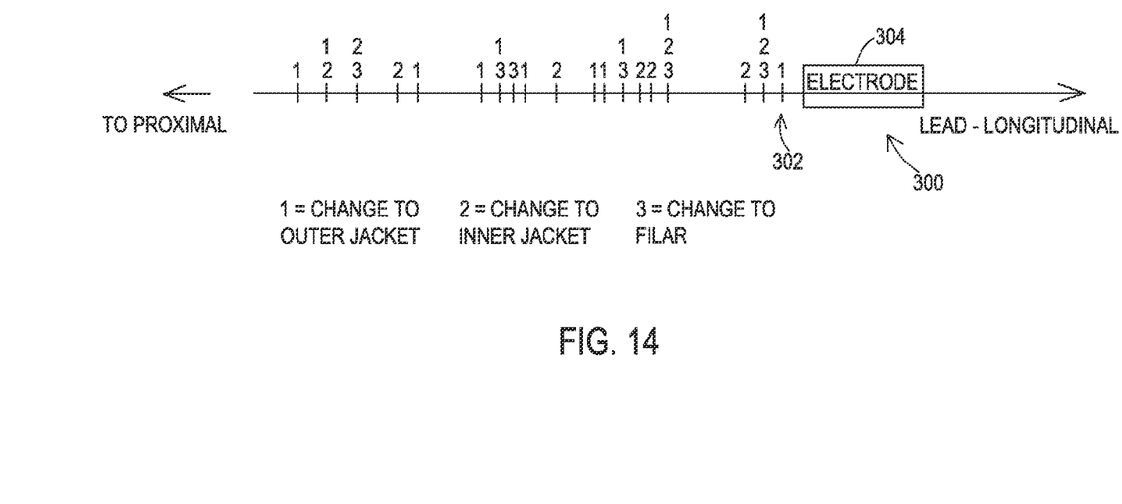
FIG. 14 shows a longitudinal distribution of reflection points in one example of a lead.

FIG. 14 shows an example of longitudinal distribution 300 of reflection points 302 along the length of a lead. It can be seen that some reflection points are created by a change only to a single element, the outer jacket (1), the inner jacket (2), or the filar (3). It can be seen that some reflection points are created by a change to two elements, the outer jacket (1) and the inner jacket (2), the outer jacket (1) and the filar (3), or the inner jacket (2) and the filar (3). Additionally, it can be seen that some reflection points are created by a change to all three elements, the outer jacket (II), the inner jacket (2), and the filar (3).

In FIG. 14 it can further be seen that in this example there is a nonstandard interval of repetition. In other words, the spacing from one reflection point to the next reflection point varies. It can also be seen in this example that there is a nonstandard interval of repetition from a reflection point involving a change to a particular element to the next reflection point involving the same element. This nonstandard interval of repetition may assist in reflecting the RF current away from the electrode and in dissipating the RF current as heat in the filar(s).

While the examples of FIGS. 2-13 show a single filar and a single inner jacket, multiple filars may be present and each filar may have a dedicated inner jacket. The physical change to the filar and/or the inner jacket may vary from filar to filar. For instance, a given reflection point involving the inner jacket (2) and/or the filar (3) as shown in FIG. 14 may pertain to one filar, multiple filars, or all filars present within a lead.

For instance, some of those reflection points of FIG. 14 may pertain to one filar while others may pertain to multiple filars.

The reflection points discussed herein may also be created by the presence of discrete circuit elements such as resistors, capacitors, and/or inductors that are electrically coupled to the filar(s). Thus, any or all of the reflection points 302 illustrated in FIG. 14 may be discrete circuit elements with non-standard intervals of repetition rather than physical changes to the filar, inner jacket, or outer jacket. For instance, there may be series resistors in-line along the filars (1), series inductors in-line along the filars (2), and/or capacitors that are parallel from the filar to floating electrodes that may have a large surface area in comparison to the stimulation electrodes and/or may be located in less critical tissue (3) that are present to vary the characteristic impedance while not adversely affecting the delivery of stimulation signals or sensed signals through the filars.

While embodiments have been particularly shown and described, it will be understood by those skilled in the art that various other changes in the form and details may be made therein without departing from the spirit and scope of the invention.

What is claimed is:

1. An implantable medical lead, comprising:
   an outer jacket;
   a filar being located within the outer jacket, the filar including physical changes with each instance of the physical change being separated from an adjacent instance of the physical change by a section having a normal physical condition where the physical changes establish multiple radio frequency reflection points located along the length of the filar;
   a proximal contact; and
   a distal electrode, the filar interconnecting the proximal contact to the distal electrode.

2. The implantable medical lead of claim 1, wherein the physical changes occur at non-standard intervals of repetition.

3. The implantable medical lead of claim 1, wherein the physical change comprises a change in filar diameter.

4. The implantable medical lead of claim 1, wherein the change in filar diameter is a reduction in filar diameter.

5. The implantable medical lead of claim 1, wherein the physical change comprises a change in a type of filar material.

6. The implantable medical lead of claim 5, wherein the change in the type of material comprises an additional filar material adjacent an existing filar material.

7. The implantable medical lead of claim 5, wherein the change in the type of material is present at the surface of the filar.

8. The implantable medical lead of claim 1, wherein the filar is surrounded by an inner jacket, the inner jacket being located within the outer jacket, the inner jacket including physical changes that establish multiple radio frequency reflection points located along the length of the filar.

9. The implantable medical lead of claim 1, wherein the outer jacket includes physical changes that establish multiple radio frequency reflection points located along the length of the filar.

10. An implantable medical lead, comprising:
    an outer jacket;
    a filar surrounded by an inner jacket, the filar and inner jacket being located within the outer jacket, the inner jacket including physical changes that establish multiple radio frequency reflection points located along the length of the filar;
    a proximal contact; and
    a distal electrode, the filar interconnecting the proximal contact to the distal electrode.

11. The implantable medical lead of claim 10, wherein the physical changes occur at non-standard intervals of repetition.

12. The implantable medical lead of claim 10, wherein the physical change comprises a change in inner jacket diameter.

13. The implantable medical lead of claim 10, wherein the change in inner jacket diameter comprises an increase in inner jacket diameter.

14. The implantable medical lead of claim 10, wherein the physical change comprises a change in a type of inner jacket material.

15. The implantable medical lead of claim 14, wherein the change in the type of material comprises a doped inner jacket material adjacent to an existing inner jacket material.

16. The implantable medical lead of claim 15, wherein the doped inner jacket material comprises multiple dopants.

17. The implantable medical lead of claim 10, wherein the filar includes physical changes that establish multiple radio frequency reflection points located along the length of the filar.

18. The implantable medical lead of claim 10, wherein the outer jacket includes physical changes that establish multiple radio frequency reflection points located along the length of the filar.

19. An implantable medical lead, comprising:
    an outer jacket;
    a filar being located within the outer jacket such that the outer jacket includes physical changes that establish multiple radio frequency reflection points located along the length of the filar at non-standard intervals of repetition;
    a proximal contact; and
    a distal electrode, the filar interconnecting the proximal contact to the distal electrode.

20. The implantable medical lead of claim 19, wherein the physical change comprises a change in outer jacket diameter.

21. The implantable medical lead of claim 19, wherein the change in outer jacket diameter comprises an increase in outer jacket diameter.

22. The implantable medical lead of claim 19, wherein the physical change comprises a change in a type of outer jacket material.

23. The implantable medical lead of claim 22, wherein the change in the type of material comprises a doped outer jacket material adjacent to an existing outer jacket material.

24. The implantable medical lead of claim 23, wherein the doped outer jacket material comprises multiple dopants.

25. The implantable medical lead of claim 19, wherein the filar includes physical changes that establish multiple radio frequency reflection points located along the length of the filar.

26. The implantable medical lead of claim 19, wherein the filar is surrounded by an inner jacket, the inner jacket being located within the outer jacket, the inner jacket including physical changes that establish multiple radio frequency reflection points located along the length of the filar.

27. An implantable medical lead, comprising:
    an outer jacket;
    a filar being located within the outer jacket;
    discrete circuit elements electrically coupled to the filar that establish multiple radio frequency reflection points located along the length of the filar at non-standard intervals of repetition, the filar including physical changes at non-standard interval of repetition that establish additional radio frequency reflection points along the length of the filar;

a proximal contact; and a distal electrode, the filar interconnecting the proximal contact to the distal electrode.

28. An implantable medical system, comprising:

an implantable medical device; and an implantable medical lead connected to the implantable medical device, the implantable medical lead comprising:

an outer jacket;

a filar being located within the outer jacket, the filar including physical changes that occur at non-standard intervals of repetition and that establish multiple radio frequency reflection points located along the length of the filar;

a proximal contact; and a distal electrode, the filar interconnecting the proximal contact to the distal electrode.

* * * * *